US012727601B2

(12) United States Patent
Caldwell et al.

(10) Patent No.: US 12,727,601 B2
(45) Date of Patent: Sep. 8, 2026

(54) SYSTEM AND METHOD FOR PROMOTING PLANT GROWTH

(71) Applicants: 3Bar Biologics, Inc., Columbus, OH (US); Ohio State Innovation Foundation, Columbus, OH (US)

(72) Inventors: Bruce H. Caldwell, Dublin, OH (US); Brian B. McSpadden Gardener, Wooster, OH (US)

(73) Assignees: 3Bar Biologics, Inc., Columbus, OH (US); Ohio State Innovation Foundation, Columbus, OH (US)

( * ) Notice: Subject to any disclaimer, the term of this patent is extended or adjusted under 35 U.S.C. 154(b) by 631 days.

(21) Appl. No.: 16/929,631

(22) Filed: Jul. 15, 2020

(65) Prior Publication Data

US 2020/0347336 A1 Nov. 5, 2020

Related U.S. Application Data

(63) Continuation of application No. 14/781,545, filed as application No. PCT/US2014/069540 on Dec. 10, 2014, now Pat. No. 10,774,298.

(Continued)

(51) Int. Cl.

| | |
|---|---|
| ***C12M 1/00*** | (2006.01) |
| ***A01N 63/20*** | (2020.01) |
| ***A01N 63/22*** | (2020.01) |
| ***A01N 63/27*** | (2020.01) |
| ***C05F 11/08*** | (2006.01) |
| ***C12M 1/04*** | (2006.01) |

(Continued)

(52) U.S. Cl.

CPC ............. *A01N 63/27* (2020.01); *A01N 63/20* (2020.01); *A01N 63/22* (2020.01); *C05F 11/08* (2013.01); *C12M 23/24* (2013.01); *C12M 23/34* (2013.01); *C12M 33/00* (2013.01); *C12M 37/00* (2013.01); *C12M 37/04* (2013.01); *C12M 45/22* (2013.01)

(58) Field of Classification Search

CPC .............................. C12M 23/34; C12M 45/22

See application file for complete search history.

(56) References Cited

U.S. PATENT DOCUMENTS

| | | | |
|---|---|---|---|
| 3,068,154 | A | 12/1962 | Majors |
| 4,941,517 | A | 7/1990 | Galloway |

(Continued)

FOREIGN PATENT DOCUMENTS

| | | | |
|---|---|---|---|
| WO | 1990015527 | A1 | 12/1990 |
| WO | 2004009756 | A1 | 1/2004 |
| WO | 2009024930 | A2 | 2/2009 |

OTHER PUBLICATIONS

Deaker et al., "Legume seed inoculation technology—a review", 2004, Soil Biology & Biochemistry, 36, pp. 1275-1288 (Year: 2004).*

(Continued)

*Primary Examiner* — Jonathan M Hurst
(74) *Attorney, Agent, or Firm* — Billion & Armitage

(57) ABSTRACT

Described herein are systems, methods and kits for culturing and applying fresh microbial inoculants in the field. The system, methods and kits are easy to use, reliable, sealed to prevent contamination, and can be stored on location, for use on demand by those unskilled in the microbiological arts. Particular embodiments described herein may be used to increase agricultural crop yields.

20 Claims, 7 Drawing Sheets

Related U.S. Application Data

(60) Provisional application No. 61/914,561, filed on Dec. 11, 2013.

(51) Int. Cl.
*C12M 1/12* (2006.01)
*C12M 1/26* (2006.01)

(56) References Cited

U.S. PATENT DOCUMENTS

| | | | | |
|---|---|---|---|---|
| 5,186,323 | A * | 2/1993 | Pfleger | B65D 81/3211 215/DIG. 8 |
| 5,507,133 | A * | 4/1996 | Singleton | C12M 45/22 53/239 |
| 6,277,625 | B1 | 8/2001 | Huang et al. | |
| 6,335,040 | B1 | 1/2002 | Hoier | |
| 2006/0053850 | A1* | 3/2006 | Lemos | C12M 23/14 71/7 |
| 2006/0154363 | A1 | 7/2006 | Horn | |
| 2009/0035856 | A1 | 2/2009 | Galliher et al. | |
| 2009/0188211 | A1* | 7/2009 | Galliher | C12M 23/14 53/434 |
| 2011/0174642 | A1 | 7/2011 | Coon | |
| 2013/0084632 | A1 | 4/2013 | Legallais et al. | |
| 2015/0264938 | A1* | 9/2015 | Gage | A01N 63/00 504/100 |
| 2017/0174642 | A1 | 6/2017 | Leban et al. | |

OTHER PUBLICATIONS

Ogut, et al., "Single and double inoculation with Azospirillum/Trichoderma: the effects on dry bean and wheat", Biol Fertil Soils, 41, 2005, 262-272.

* cited by examiner

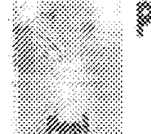
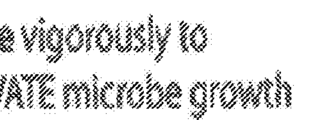
FIG. 2

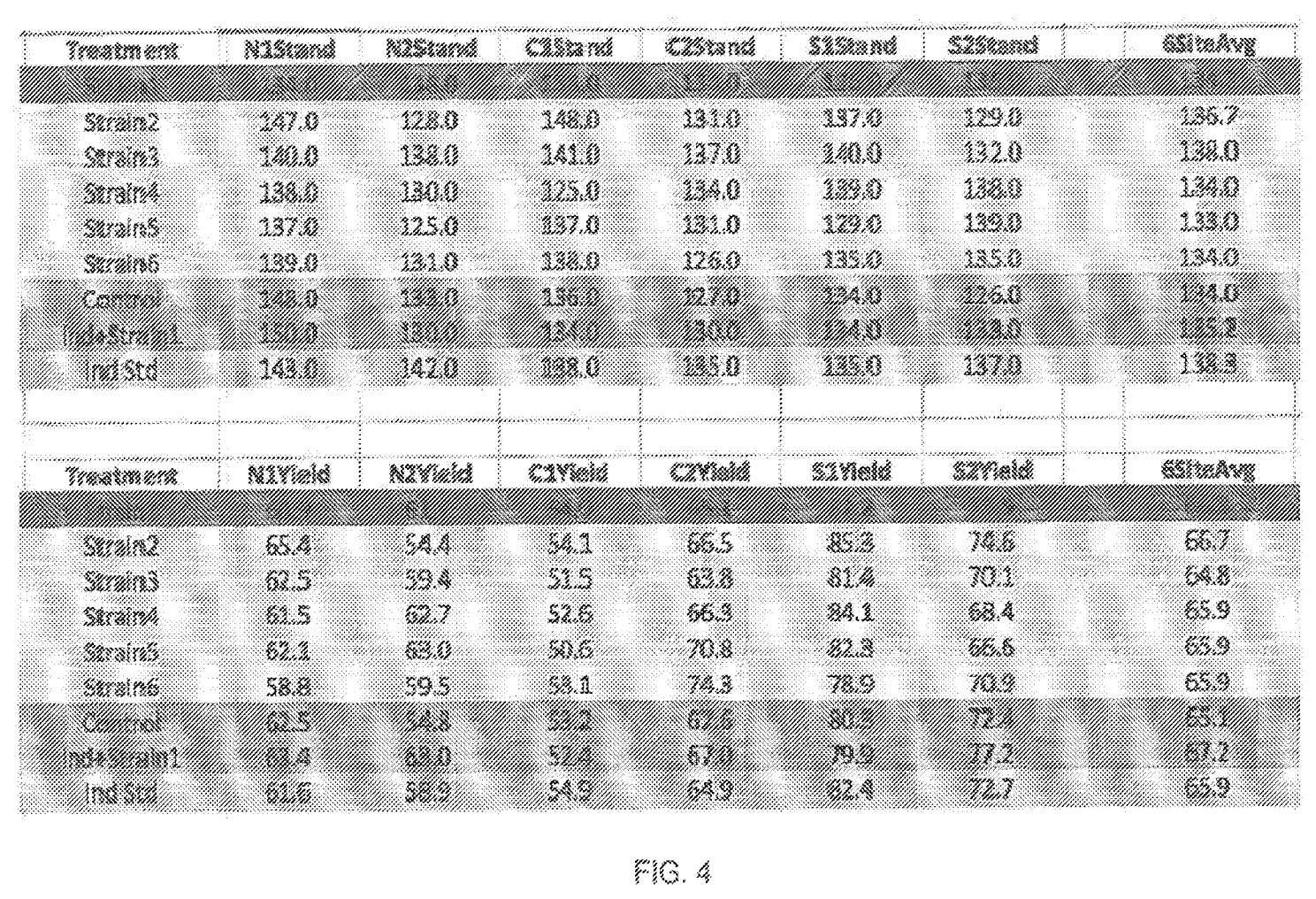

| Treatment | N1Stand | N2Stand | C1Stand | C2Stand | S1Stand | S2Stand | | 6SiteAvg |
|---|---|---|---|---|---|---|---|---|
| [illegible] | [illegible] | [illegible] | [illegible] | [illegible] | [illegible] | [illegible] | | [illegible] |
| Strain2 | 147.0 | 128.0 | 148.0 | 131.0 | 137.0 | 129.0 | | 136.7 |
| Strain3 | 140.0 | 138.0 | 141.0 | 137.0 | 140.0 | 132.0 | | 138.0 |
| Strain4 | 138.0 | 130.0 | 125.0 | 134.0 | 139.0 | 138.0 | | 134.0 |
| Strain5 | 137.0 | 125.0 | 137.0 | 131.0 | 129.0 | 139.0 | | 133.0 |
| Strain6 | 139.0 | 131.0 | 138.0 | 126.0 | 135.0 | 135.0 | | 134.0 |
| Control | 148.0 | 133.0 | 136.0 | 127.0 | 134.0 | 126.0 | | 134.0 |
| Ind+Strain1 | 150.0 | 130.0 | 134.0 | 130.0 | 134.0 | 133.0 | | 135.2 |
| Ind Std | 143.0 | 142.0 | 138.0 | 135.0 | 135.0 | 137.0 | | 138.3 |

| Treatment | N1Yield | N2Yield | C1Yield | C2Yield | S1Yield | S2Yield | | 6SiteAvg |
|---|---|---|---|---|---|---|---|---|
| [illegible] | [illegible] | [illegible] | [illegible] | [illegible] | [illegible] | [illegible] | | [illegible] |
| Strain2 | 65.4 | 54.4 | 54.1 | 66.5 | 85.3 | 74.6 | | 66.7 |
| Strain3 | 62.5 | 59.4 | 51.5 | 63.8 | 81.4 | 70.1 | | 64.8 |
| Strain4 | 61.5 | 62.7 | 52.6 | 66.3 | 84.1 | 68.4 | | 65.9 |
| Strain5 | 62.1 | 63.0 | 50.6 | 70.8 | 82.3 | 66.6 | | 65.9 |
| Strain6 | 58.8 | 59.5 | 53.1 | 74.3 | 78.9 | 70.9 | | 65.9 |
| Control | 62.5 | 54.8 | 53.2 | 67.6 | 80.2 | 72.4 | | 65.1 |
| Ind+Strain1 | 63.4 | 68.0 | 52.4 | 67.0 | 79.9 | 77.2 | | 67.2 |
| Ind Std | 61.6 | 58.9 | 54.9 | 64.9 | 82.4 | 72.7 | | 65.9 |

FIG. 4

| Treatment | CRStand | DRStand | MAStand | VWStand | FAStand | WYStand | 6SiteAvg |
|---|---|---|---|---|---|---|---|
| Strain1 | 357 | 350 | 365 | 364 | 359 | 362 | 359.5 |
| Strain2 | 361 | 366 | 359 | 362 | 366 | 366 | 363.3 |
| Strain3 | 360 | 367 | 355 | 337 | 356 | 353 | 356.0 |
| Strain7 | 365 | 359 | 362 | 358 | 360 | 362 | 359.3 |
| Comm7 | 354 | 359 | 352 | 346 | 367 | 362 | 356.7 |
| Control | 361 | 359 | 358 | 344 | 364 | 349 | 355.2 |
| Ind+Strain1 | 367 | 359 | 359 | 360 | 367 | 363 | 362.5 |
| Ind Std | 355 | 358 | 359 | 364 | 356 | 363 | 359.2 |

| Treatment | CRYield | DRYield | MAYield | VWYield | FAYield | WYYield | 6SiteAvg |
|---|---|---|---|---|---|---|---|
| Strain1 | 224.1 | 213.3 | 220.4 | 246.6 | 251.6 | 221.9 | 229.6 |
| Strain2 | 222.2 | 200.4 | 220.3 | 259.4 | 258.8 | 226.1 | 229.2 |
| Strain3 | 229.4 | 205.1 | 221.8 | 222.6 | 259.6 | 213.3 | 225.6 |
| Strain7 | 234.1 | 217.3 | 229.2 | 238.8 | 264 | 222.9 | 234.2 |
| Comm7 | 221.2 | 213.8 | 215.8 | 229.4 | 259 | 204.6 | 224.6 |
| Control | 230.9 | 202.2 | 218.6 | 222.6 | 254.7 | 214.9 | 224.0 |
| Ind+Strain1 | 226.8 | 215.3 | [illegible] | [illegible] | 250.8 | 212.3 | 227.7 |
| Ind Std | 227.5 | 215.4 | 220.4 | 241.3 | 251.5 | 218.5 | 229.1 |

FIG. 5

| Treatment | Yield |
|---|---|
| Strain applied On-Farm | 148.4 |
| Untreated Check | 141.8 |

FIG. 6

SYSTEM AND METHOD FOR PROMOTING PLANT GROWTH

CROSS REFERENCE TO RELATED APPLICATIONS

This application is a continuation of U.S. application Ser. No. 14/781,545 filed Sep. 30, 2015, which is the National Stage Application of PCT/US14/069540, filed Dec. 10, 2014, which claims the benefit of U.S. Provisional Application No. 61/914,561, filed Dec. 11, 2013, the contents of which are incorporated herein by reference A claim of priority to all, to the extent appropriate, is made.

BACKGROUND OF THE INVENTION

Producers have long used beneficial microbial cultures to seeds, seedlings, soils and/or plants to reduce various biotic and abiotic stresses that significantly limit crop yields. These microbial cultures are commercially available as inoculant products that are distributed as dry powders or in bulk liquid form to the producers for end-use application. Such distribution of the inoculant products often subjects the microbial cultures to environmental abuse which, in turn, introduces undesirable variability in culture viability and physiological activity at the time of application. Stabilization of cells through formulation and spore formation does not adequately preclude cell death during manufacturing and distribution of such inoculants, leading to a decrease in effectiveness and reliability of the inoculants.

Microbial inoculant products can experience significant declines in population during their limited shelf life. This is a source of a significant amount of waste in materials, water, and energy relative to the benefits supplied by such products. Current microbial products are typically fermented in large centralized manufacturing facilities, then concentrated and/or centrifuged in order to increase populations above the label values, thereby allowing the manufacturers to account for the death of viable organisms during shipping and storage. Other attempted solutions to reduce loss of microbial inoculant viability include introducing ingredients to the bulk liquid culture to retard microbial metabolism and oxidation, putting the cells in an essentially inactive state for packaging and distribution. Thus, a significant problem in the expanding biologicals market sector is the inconsistent performance in the field of such inoculant products resulting from low levels of initial activity and/or low percent cell viability at the time of application.

Most inoculant products in the market today tend to have sub-optimal performance in many locations, due at least in part to the fact that such available inoculant products use microbes that are not well adapted to local conditions. Often, the success of a particular inoculant product can depend on the plant species and cultivar to which the inoculant product is applied. Also, the adaptability of the microbe in the inoculant product to local soil conditions and the ability to establish beneficial microbe populations around the plant zone can also affect the success and usefulness of the inoculant. However, microbial inoculant products use microbes that have been selected more on the basis of ability to survive the delivery supply chain than in-field performance. For example, many inoculant products contain spore formers such as *Bacillus* spp. and *Trichoderma* spp. that have some ability to survive harsh conditions of distribution and storage, but may not provide the optimal results desired for end use applications. While non-spore formers such as *Pseudomonas* spp. have been shown to have beneficial effects on multiple crops, use of such non-spore formers have not achieved widespread distribution due to incompatibility with current distribution methods.

Since the inoculant products contain living organisms, how the inoculant products are prepared, and then applied, can significantly affect the outcome. There is a need for systems and methods for providing easy-to-use, reliable, and viable microbial inoculants.

SUMMARY OF THE INVENTION

Described herein are microbial inoculant systems, having: at least one first chamber configured to contain a predetermined amount of microbes in a sealed manner; and, at least one second chamber configured to contain a predetermined amount of a medium suitable for growing the microbes to substantially a log phase growth stage. The first chamber is separated from the second chamber by at least one dividing member. The integrity of the dividing member is capable of being disrupted so as to allow the microbes and medium to be combined. The second chamber is configured to remain in a sealed condition upon disruption of the integrity of the dividing member, and during the log phase growth stage of the microbes.

In certain embodiments, the microbes, when present in the first chamber, are not present in a log phase growth stage.

In certain embodiments, the microbes, when present in the first chamber, are in a form selected from one or more of: planktonic, biofilmic, dormant, lyophilized, partially dormant, partially lyophilized, sporulated, dehydrated, and freeze-dried; and, wherein the microbes are not present in a log phase growth.

In certain embodiments, the system further includes at least one device for disrupting the integrity of the dividing member.

In certain embodiments, the dividing member is configured to form at least one common wall between the first chamber and the second chamber. In certain embodiments, the first chamber is removably connected to the second chamber. In other embodiments, the first chamber can be within the second chamber. In other embodiments, the first chamber is fixedly connected to the second chamber.

In certain embodiments, at least the second chamber is sealed to resist environmental contamination during the log phase growth stage of the microbes.

In certain embodiments, at least one of the first chamber and the second chamber has a modified atmosphere.

In certain embodiments, at least one of the first chamber and the second chamber has at least one gas permeable member. For example, in certain embodiments, oxygen is present in the second chamber, as a percentage of total gas in the second chamber, in a percentage selected from: about 0.5% to about 100%; and about 5% to 25% oxygen.

In certain embodiments, the medium comprises one or more of: water, non-chlorinated water, distilled water, Luria broth, and nutrient broth. In certain embodiments, the percent of media in the second chamber, as a function of total volume of the second chamber, is a percent selected from: from about 10% to about 95%; and from about 35% to about 65% liquid.

In certain embodiments, at least one of the first chamber and the second chamber includes at least one access port for connection to a delivery device.

In certain embodiments, at least one of the first chamber and the second chamber includes at least one access port for connection to a dilutor or a sprayer.

In certain embodiments, the dividing member has a quality selected from the group consisting of: tearable; frangible; puncturable; rupturable; dissolvable; and movable.

In certain embodiments, the system further includes at least one means for disrupting the integrity of the dividing member by tearing, puncturing, rupturing, cutting, dissolving, and/or moving.

In certain embodiments, the microbes are selected from the group comprising one or more of: bacteria, yeast, fungi, algae, protozoa, and, nematodes. For example, the microbes can comprise one or more of: *Achromobacter, Actimomycetes, Arthrobacter, Azospirillum, Azotobacter, Bacillus, Bradyrhizobium, Chromobacterium, Cyanobacteria, Enterobacter, Gliocladium, Klebsiella, Lysobacter, Methylobacterium, Mitsuaria, Paenibacillus, Pasteuria, Pseudomonas, Rhizobium, Serratia*, and *Streptomyces*. In other embodiments, the microbes can comprise one or more of: *Penicillium, Trichoderma, Chaetomium*, mycorrhizal fungi, and those forming ectomycorrhizae and vesicular-arbuscular mycorrhizae; mycoparastic fungi, nematode-trapping fungi, avirulent isolates of pathogenic fungi or bacteria. In one embodiment, the microbes can comprise one or more of: 2, 4-diacetylphloroglucinol (DAPG)-producing bacteria; and ph1D+ *Pseudomonas* spp. Also, in certain embodiments, the microbes can be derived from yield improving indigenous soil microflora from a predetermined location.

In another broad aspect, there is provided herein a method of culturing microbes, comprising: i) disrupting the integrity of a dividing member that separates a first chamber and a second chamber so as to introduce a predetermined amount of microbes stored in the first chamber into a media stored in the second chamber, and ii) culturing the microbes introduced into the second chamber under conditions suitable for rapid growth of the microbes.

In certain embodiments, the method of culturing microbes comprises: i) disrupting the integrity of the dividing member so as to introduce the predetermined amount of microbes stored in the first chamber into the media stored in the second chamber, and ii) culturing the microbes introduced into the second chamber under conditions suitable for rapid growth of the microbes.

In certain embodiments, the method of culturing microbes comprises: i) providing a predetermined amount of microbes in a sealed first chamber; ii) providing a predetermined amount of a medium suitable for growing the microbes to substantially a log phase growth stage in a sealed second chamber; the first chamber being separated from the second chamber by at least one dividing member; iii) disrupting the integrity of the dividing member so as to allow the microbes and medium to be combined; and, iv) allowing the second chamber to remain in a sealed condition upon disruption of the integrity of the dividing member until a log phase growth stage of the microbes is achieved.

Further, in certain embodiments, the method further comprises storing the first and second chambers for a predetermined amount of time before disrupting the dividing member. Still further, in certain embodiments, the method includes a step where the second chamber is unsealed after the log phase growth stage is reached. In yet further embodiments, the method further including a step of applying the log phase growth microbes to one or more of seeds, seedlings, plants, and soil.

In certain embodiments, the culturing is at temperature range selected from: about 10° C. to about 60° C.; about 20° C. to about 50° C.; about 18° C. to about 27° C.; about 30° C. to about 40° C.; about 37° C.; about 25° C., and ambient temperature.

In certain embodiments, the culturing is for a time of: at least about 0.5 day to at least about 21 days; at least about 1 day to at least about 14 days; at least about 1 day to at least about 7 days; at least about 1 day; and, at least about 7 days.

In another broad aspect, there is provided herein a method of treating seeds, seedlings, plants, or soil, comprising: applying cultured microbes produced according to the methods described herein to seeds, seedlings, plants, or soil.

In certain embodiments, the method can further comprise diluting the cultured microbes prior to applying.

In certain embodiments, the method can further comprise drying the seeds and/or soil after applying the cultured microbes to the seed and/or soil.

In certain embodiments, the microbe culture is diluted to a cell number of about 1,000 to about 10,000,000 CFUs per ml in the target diluents.

In certain embodiments, applying is via spraying at a rate of about $10^3$ cells/ml to about $10^7$ cells/ml. For example, the method can include wherein applying results in about 1000 cells/seed, seedling, plant, or square inch of soil, to about 10 million cells/seed, seedling, plant, or square inch of soil.

In certain embodiments, the seeds, seedlings or plants are leguminous seeds, seedlings, or plants such as soybeans.

In certain embodiments, the seeds, seedlings, or plants are grain crops, such as corn.

In certain embodiments, the seeds, seedlings, or plants are vegetables such as tomato or flowers such as petunias.

In yet another broad aspect, there is provided herein a kit, comprising: the system as described herein; and instructions on how to produce cultured microbes using the system.

Various objects and advantages of this invention will become apparent to those skilled in the art from the following detailed description of the preferred embodiments, when read in light of the accompanying drawings.

BRIEF DESCRIPTION OF THE FIGURES

FIG. 2: Example of label and instructions for use. The easy to use format of the system described herein allows one unskilled in the microbiological arts to readily prepare microbial inoculant cultures for use in agriculture.

FIG. 4: Beneficial effects of inoculants prepared in the bioreactor system described herein when applied to soybeans. Bioreactors were constructed with different beneficial bacterial strains and delivered to cooperators for use as soybean seed treatments (see Table 1 for strain identities). Cooperators activated the bioreactors 1 to 7 days prior to treating and planting seed according to label directions (FIG. 2) at six different locations (N1, N2, C1, C2, S1, and S2). Experiments were established in a randomized complete block design with four replicates per treatment at each location. Crop stands (×1000 plants per acre) and yields (bushels per acre) were measured independently at the six different field locations. Across this six-site trial, soybeans treated with inoculants made from the bioreactors had comparable stands but higher yields than the control in five of the six embodiments. Yield increases for those same five treatments were as good or better than an industry standard (Ind Std) seed treatment (TMGerm). Combining Strain 1 with the industry standard seed treatment resulted in further increases in yield.

FIG. 5: Beneficial effects of inoculants prepared in the bioreactor system describe herein when applied to corn. Bioreactors were constructed with different beneficial bacterial strains and delivered to cooperators for use as corn seed treatments (see Table 1 for strain identities). Cooperators activated the bioreactors 1 to 7 days prior to treating and planting seed according to label directions (FIG. 2) at six different locations (CR, DR, MA, VW, FA, and WY). Experiments were established in a randomized complete block design with four replicates per treatment at each location. Crop stands (δ×100 plants per acre) and yields (bushels per acre) were measured independently at the six different field locations. Across the six locations, corn treated with the inoculants made from the bioreactors had higher stands and yields than the control in at least four of the six test locations. Corn treated with inoculants made from the bioreactors had higher stands and higher yields than the control, on average. Yield increases for three of the four test treatments were as good or better than an industry standard (Ind Std) seed treatment (TMGerm). When Strain 1 was combined with the industry standard seed treatment, further increases in yields were observed. And, while the commercially available formulant of strain 7 (Comm7) did increase the six site average stands and yields of corn, higher stands and yields were obtained with the same strain formulated in the prototype bioreactor (Strain7) indicating that the bioreactor delivers a more effective dose of the microbial inoculant.

FIG. 6: Beneficial effects of inoculants prepared in the bioreactor system described herein when applied to corn in a typical farming operation. Product was activated by the farmer according to the instructions in FIG. 2. Product was applied at planting as a strip and the location was marked with field flags. At harvest, yield of both the test strip and an adjacent untreated check strip was measured using a weigh wagon. The data showed a test strip yield 4.6% higher than that of the untreated check.

DETAILED DESCRIPTION OF THE INVENTION

Figure 1A:
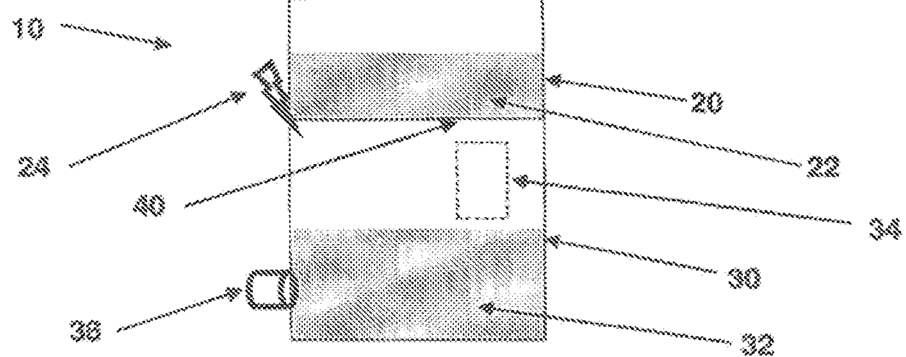
FIG. 1: Schematic illustrations and photographs of an example unified microbial inoculant delivery system. The diagrams (FIGS. 1A and 1B) show two contrasting configurations of the two chambers described herein.
FIG. 1C presents a photo showing a system prior to (left) and three days after (right) activation. Turbid bacterial growth in the second chamber (right) indicates saturating (i.e. completion of log phase) growth of the microbial culture.
FIG. 1D presents a photo showing an example of a microbial chamber 1 before and after sealing (left), the sealing apparatus (center), and a range of activated bioreactors demonstrating turbid microbial growth (right).

Described herein is a convenient and reliable cell culture system that is useful in preparing seed and plant, including seedling (hereinafter "crop") inoculants, but may also be used for a variety of cell culturing purposes. Also provided are methods for inoculating a crop. One benefit is that an individual may culture microbial inoculants on demand, without specialized knowledge of culturing theory or techniques, at a convenient time, and in a sealed container free from external contamination. Moreover, the inoculants that result from the use of the present system are reliably viable and active at the time of use. The on-demand nature of the presently described system greatly reduces waste. The use of the presently described system encourages economically- and ecologically-efficient applications of the microbial culture. Using a standardized bioreactor design, the microbial culture can be more readily selected for a particular microenvironment, crop, and desired result. Optionally, the crop inoculants can be diluted and applied in a unitary system container, with the added benefit of assuring application of the inoculant that is essentially free of contamination.

Further in use, the end-user shakes the mixture and stores the system for a prescribed time/temperature condition (e.g., ambient conditions for 18-72 hours) to establish a substantially stationary phase culture that has completed log phase active growth. The operator then has a prescribed window of time (e.g., 1-7 days post activation) in which to distribute the inoculant onto the desired seed, soil, or plants with or without further dilution in water. The system described herein also allows for the ability to easily achieve the dilution and distribution by connecting the reacting vessel to a dilution/dispensing sprayer or drip system for easy application to seeds, plants or soil.

The system and methods described herein enables the field use of beneficial microbes that are not capable of surviving typical manufacturing and distribution supply chains currently found in industry. Use of the system described herein also increases the potential population of microbes currently marketed, by pushing the log phase growth stage downstream, much closer to the end product use such that the microbial culture is not substantially dormant or dead, conditions typically encountered by current users of microbial products.

The system described herein is disposable, easy to use by an unskilled operator, and ensures that the microbial growth phase occurs in a sterile environment at a precise ratio with media. This achieves a level of freshness previously unobtainable, which is a highly desirable characteristic for agricultural inoculants and, in fact, many different types of products that involve a living microbe to achieve their efficacy.

The bioreactor system, microbial inoculants, and kits described herein may be useful in the propagation, farming, or raising of dicotyledonous vegetables and fruit, monocotyledonous grain crops, ornamental bedding crops, and turf grass.

Microbial Inoculants

The term "microorganisms, "microbes", "microbial inoculant", or "microbial culture" as used herein encompasses bacteria, fungi (including yeast), algae, protozoans and viruses. The term "bacteria" as used herein encompasses bacteria, bacteria-like organisms, and their equivalents, including actinomycetes.

The term "beneficial" as used herein refers to microbes that, on balance, provide a greater benefit to the plant than any harm they may cause. The determination of whether such a microorganism will benefit the plant can be made by those skilled in the art by considering any one or more of a multitude of factors. These include, but are not limited to: 1) rendering nutrients more available or in greater amounts; 2) enhancing or inducing resistance to pathogens; 3) producing a desired chemical, such as a pesticide, itself or by conversion of plant metabolites; 4) conferring or enhancing stress tolerance; 5) increasing metabolic efficiency, such as photosynthetic efficiency, and 6) inactivating toxins.

Beneficial Microbes

Understanding the strengths, requirements, limitations and general biology of a beneficial microbe is important for obtaining the greatest benefits from its use. In many current agricultural practices, large numbers of cells of commercially available microbes are added to the soil by mixing in granules or by drenching before pathogen pressure is high. Knowing the environmental conditions under which the beneficial microbe performs best can help ensure the inoculants promote the health and protection of the plant. Alternatively, the addition of metabolically active microbes can help to ensure that their beneficial activities are expressed in a timely way. Additionally, compatibility with the crop production system and grower inputs is to be taken into consideration for the proper use of beneficial microbes. Soil pH, temperature, humidity, soil or container media composition, and target plant tissue (root, tuber, etc.) all affect the establishment of beneficial microbes in the soil. Also important are how pesticide inputs, nutrient inputs, irrigation method and frequency, plant growth regulators (PGRs), and the like may affect beneficial microbe performance or longevity. Information about environmental and production input compatibility and phytotoxicity information may also be helpful.

Also, in certain situations, the longevity of a beneficial microbe or microbes in the soil or potting mix environment can promote the health of crops over a longer time course. Bacteria tend to release their protective secondary metabolites for up to 4 weeks after application, even though they may persist in the soil environment longer. Fungi tend to survive longer with protection documented for up to 12 weeks.

Diverse microbes may express beneficial effects when applied to soils, seeds, or plants. Such microbes may include, for example, bacteria belonging to the genera *Achromobacter, Actimomycetes, Arthrobacter, Azotobacter, Azospirillum, Bacillus, Bifidobacterium, Brevibacillus, Bradyrhizobium, Burkholderia, Chitinophaga, Chromobacterium, Chryseobacterium, Curtobacterium, Cyanobacteria, Enterobacter, Exiguobacterium, Janthinobacter, Klebsiella, Lactobacillus, Lysobacter, Methylobacterium, Mitsuaria, Novosphingomonas, Paenibacillus, Pantoea, Pasteuria, Pseudomonas, Rhizobium, Serratia, Sinorhizobium Sphingomonas, Stenotrophomonas*, and *Streptomyces*. The microbe might also be fungi or fungal yeasts, including but not limited to the following genera: *Alternaria, Aspergillus, Beauvaria, Chaetomium Coniella, Epicoccum, Fusarium, Glioclasidum, Glomus, Gigaspora, Lasiodiplodia, Myrothesium, Paecilomyces, Penicillium, Phlebioposis, Phoma, Saccharomyces*, and *Trichoderma,*

Inoculants may use native or non-native microbes. However, it is ecologically more sensible to use strains that are native to the growing region to which they are to be applied as inoculants, or at least to the crops and/or soil conditions that closely reflect their geographical origins. Such microbes can be introduced to the plants or seeds by the use of inoculant compositions. The process by which inoculant compositions are created includes the step of culturing the microbes, generally in a liquid media, as described herein.

Stable Microbial Cultures

Stable microbial cultures generally refers to a population of microbes that are in a state where they are preserved, allowing for long-term storage with minimal death. Stable microbial cultures include cultures that are dormant, planktonic, biofilmic, freeze-dried, lyophilized, sporulated, or dehydrated, and are not experiencing log phase growth. Someone skilled in the microbiological arts will have the capacity to prepare stable cultures from larger batches of microbial cells grown on solid or liquid media.

In general, the microbes can be initially grown on a variety of suitable nutrient media. Preferably, the microbe is grown using a composition that has been shown to be optimal for that particular genus and species of microorganism. Suitable nutrient or growth media generally contains, in addition to a carbon source, other nutrients, such as, for example: a nitrogen source; sources of sulfur and phosphorus; inorganic materials such as trace metals; growth factors; oxygen and carbon dioxide. The nutrient media generally can be prepared from commercially available materials suitable for the microbes being stabilized, e.g., Bacto Nutrient Broth. Such suitable nutrient media and growth conditions applicable to particular microbial strains are evident to one skilled in this art. For example, bacteria generally are capable of growing over a wide range of physical conditions and are capable of utilizing many different nutrients, noting that optimal growth may require certain specific conditions for a given species.

In a preferred embodiment, microbes are grown in a laboratory and, under axenic conditions, stabilized on a solid matrix that is then sealed in a first chamber to be released, on the demand of the consumer, into a second chamber to initiate active growth immediately prior to use. Specifically, described herein is a system that allows for the use of precise amounts of media and stable microbial cultures for a desired end-use (e.g., seed, soil, or plant treatment). The media and stable microbial cultures are held in sealed chambers separated by a dividing member. When the fresh microbial inoculants are needed by the end-user for application to seeds, plants, or for other field applications, an individual unskilled in microbiology techniques can break, remove, or reposition the member or dividing member so that the stable microbial cultures are mixed with the media to initiate growth (i.e., activate the bioreactor).

The system can be configured to allow appropriate gas exchange to allow for appropriate growth conditions of the microbial cultures, or alternatively the system can be filled with oxygen during manufacturing, or the system can be provided with an oxidizer (e.g., $H_2O_2$ or super oxygenated water) to provide appropriate oxygen levels to support log phase growth of aerobic microbes. Also, in certain embodiments, one or more of the chambers may be filled with a modified atmosphere having a particular type and amount of gas suitable to the particular microbe to be grown. One of ordinary skill in the art would know what type and amount of gases is suitable for rapid growth of various types of microbes. In particular embodiments, the amount of media used is such as to allow for proper gas exchanges to support a stable culture in a first chamber and logarithmic growth in a second chamber following activation. By keeping the entire system enclosed, the resulting microbial inoculants are substantially free of contaminants that would typically decrease the viability and effectiveness of the inoculant.

Microbial Growth

For successful microbial culturing, generally these features are present: 1) suspension of the microbes in the media, and 2) aeration of the media to support growth of the microbe. Proper suspension of microbes in the media helps with aeration, i.e., good contact of the microbe with dissolved gases in the media. Good suspension is also important for the microbes' access to the nutrients and other growth factors in the culture media. Proper aeration involves ensuring that there are sufficient dissolved gases in the media to support growth of the microbe. The term "aeration" is used in the present specification with reference to aerobic organisms, which may be cultured in the presently described system. However, persons skilled in the art will appreciate that proper gas exchange for anaerobic organisms is also important, and the term "aeration" as used herein is considered to encompass gas exchange of any type.

It is well understood that there are several phases of microbial growth. During a lag phase, the microbes adapt themselves to growth conditions, where the microbe is maturing but not yet able to divide. The next phase is a log phase, which is a period characterized by repeated cell doubling, where the number of new bacteria is proportional to the present population. If growth is not limited, the rate of population increase doubles with each consecutive time period. This log phase is also referred to as an exponential growth phase. Following the log phase is a stationary phase, often caused by growth limiting factors such as depletion of nutrients, followed by a death phase where the microbes run out of nutrients and begin to die. The incubation periods to achieve each stage of growth generally depends on such factors such as the microbes themselves, the type of media used to grow the microbes, and the temperature at which the microbes are grown. Microbes in the late log and early stationary phases growth are the most robust, and microbes will be the most effective if applied in this range. The presently described system is capable of providing a desired amount of healthy inoculants in early stationary phase, as compared to other currently used methods. A substantial number of commercially available inoculants consist of concentrated cultures of cells formulated and stored in dormant and/or death phases.

The incubation conditions to achieve substantially late log/early stationary phase growth to provide the most effective microbial inoculants generally will vary depending on the microbe itself, the amount of stable microbial culture to be added, the type and amount of media added to the cell culture chamber, and the temperature at which the microbes are grown. One of skill in the art would be able to determine the appropriate amount of stable microbial inoculants and media, the appropriate incubation temperature and the appropriate incubation period to reach substantially late log/early stationary phase growth for a given bioreactor design. For example, depending on such factors as described above, the incubation periods can be from at least about half a day to about 21 days, from about 1 day to about 15 days, or between about 1 day and about 7 days. It is to be understood that such incubation times will vary depending on the specific microbe, the final volume of the microbial inoculant required, the incubation temperature and the type of media used.

Likewise, the incubation temperature also varies depending on the type of microbe involved; for example, bacteria tend to have maximum growth rates ranging from 15 to 45° C. In various embodiments, the temperature can be from about 10° C. to about 60° C., with preferred embodiments being incubated between 18 and 30° C. In certain embodiments, the incubation is performed at ambient temperature such that there is ease of use for the end user (who may not have access to a temperature controlled environment for incubation).

Media

By "media," "growth media," "culture media," and "nutrient media," it is meant liquid that supports the growth of the microbes. Microbes are extraordinarily diverse in their requirements for growth. Microbes are greatly affected by environmental conditions and will grow in accordance to how these environmental niches support their individual needs. Factors that affect microbial growth include but are not limited to, pH, osmolality, water activity, temperature, and oxygen levels. There is a great deal of nutritional diversity among microbes; therefore, microbial growth is greatly affected by the nutrients that are available in their environment.

The type and amount of media to support substantially log phase growth of the microbe will depend on the microbe itself. Care must be taken as to not add too much nutrients to stimulate high rates of metabolism in the microbe that could disturb growth rates. One of skill in the art would be able to determine the appropriate media for culturing a particular microbe so as to achieve substantially late log phase/early stage growth for a given bioreactor design. The type of media will depend on the type of microbe being grown. Liquid media can be water, or a nutrient solution with factors that aid in the growth of the microbes. The appropriate nutrient source(s) should be selected for each microbe strain to be produced. For most rhizobial cultures, for example, it has been found that a nutrient composition of yeast extract and mannitol produces exemplary results. For other bacterial cultures, commercially available nutrient broths may be used successfully. For many fungal cultures and some bacterial cultures, wheat and bran flour in general, and conventional white unbleached wheat flour in particular, have been found advantageous for use as a nutrient sources and could be provided as axenic slurries or suspensions.

The amount of media added to the cell culture chamber will vary depending on the microbes to be cultured and the amount of aeration required for a particular microbe. Sufficient space in the cell culture chamber will allow for gas exchange in the media to support proper growth of the microbe. The range of percentage of media that fills the first chamber can range from about 10% to about 95%, with particular embodiments ranging from 35% to 65%.

Information regarding various growth media, incubation times, and handling of microbes can be found in *Microbiology: A Laboratory Manual* (*9th Edition*), *Benjamin Cummings, Handbook of Microbiological Media, 2$^{nd}$ Edition*, CRC Press, and *Laboratory Exercises in Microbiology, Ninth Edition*, Harley, McGraw-Hill Science/Engineering/Math, which are expressly incorporated by reference.

Unitary System

The system described herein has been designed and tested for use by those unskilled in the art of microbiology (FIG. 1). Referring now to the schematic illustrations shown in FIG. 1A, a unitary microbial storage/culture system 10 includes a first sealable chamber 20 that is configured for storing a stabilized microbial culture 22, and a second sealable chamber 30 that is configured for holding a desired media 32. The first chamber 20 is separated by a dividing member 40 from the second chamber 30. In the embodiment shown in FIG. 1A, the dividing member 40 defines at least one wall of the first chamber 20.

The second chamber 30 contains oxygen and optionally other gasses as well as media, particularly liquid media 32. In certain embodiments, the second chamber 30 can include one or more accesses to oxygen and other gasses via a gas permeable member 34. In certain embodiments, at least one of the first chamber and the second chamber includes at least one access port 36 for connection to a delivery device, such as dilutor or a sprayer.

The system 10 provides an "on-demand" method for providing "fresh" or "substantially late log/early stationary phase" microbes at a time that is most advantageous for the end-user. In use, when the integrity of dividing member 40 is disrupted, the stabilized microbial culture 22 is dispersed into the media 32. It is to be understood that such disruption can be accomplished in various manners. For example, the dividing member 40 may be tearable, cuttable, frangible, puncturable, rupturable, dissolvable, and/or movable. In one embodiment, the dividing member can be a frangible member capable of being broken by application of a force. For example, U.S. Pat. No. 8,443,970 describes a frangible member cup having an ingredient within the cup and having a diaphragm button operably attached to a stake with the stake's sharp point at one end and the diaphragm button at the opposing end. Pushing the diaphragm moved the stake to break the frangible member to allow the contents of the diaphragm to freely pass into another chamber containing liquid.

In other embodiments, one or more of the first chamber and the second chamber can have grooved threads to allow the first chamber to be affixed to, or removed from, the second chamber. Additionally, other grooved members can be affixed to, or removed from, the first and/or second chamber to aid in dilution and application (e.g., attaching to a dilution or spraying mechanism).

In other embodiments, a piercing device 24 can be affixed to the first and/or second chambers opposing the dividing member 40 to break the dividing member 40. In another alternative embodiment, the piercing device 24 can be a bead or a ball bearing that can be added to one or more of the first and second chambers, such that when shaken vigorously, the bead or ball bearing is capable of breaking the dividing member, thereby mixing the contents of the first chamber and the second chamber. The dividing member can be strong enough to withstand normal handling, but able to be broken only when vigorous shaking occurs.

The dividing member could also be made of a partially dissolvable material that could withstand small exposure to the liquid media that may occur during normal handling, but when vigorously shaken, the partially dissolved dividing member would become unstable and break.

Alternatively, where the first chamber and the second chamber are in contact with each other, and share a common wall, and the dividing member spans a space between the two, the dividing material can be made of a malleable material, with an elongated tear spanning the space. The malleable dividing material can be stretched apart to break, and allow the stable microbes in the first chamber to freely pass into the second chamber.

Figure 1B:
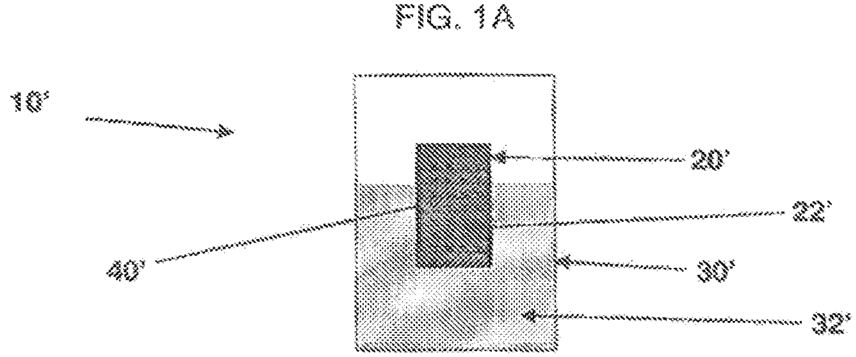

Alternatively, as shown in the embodiment in FIG. 1B, a unitary microbial storage/culture system 10' includes a first sealable chamber 20' that is configured for storing a stabilized microbial culture 22', and a second sealable chamber 30' that is configured for holding a desired media 32.' The first chamber 20' is separated by a dividing member 40' from the second chamber 30. In the embodiment shown in FIG. 1B, the dividing member 40' defines at the entire first chamber 20'. In such embodiment, the dividing member 40' can be frangible material (e.g. glass, plastic), and the second chamber can be malleable material allows the end-user to grip the frangible material and break it, thereby releasing the microbes 22' into the media 32', without exposing the second chamber 30 to external contaminants. The malleable material can be strong enough to not be ruptured or punctured, but capable of being shaped by an external handler to allow handling without exposing the inside to contaminants.

Other alternatives of movable dividing members known in the art may also be applied, such as dividing members that can be moved to open the two chambers to each other to allow mixing of the stable microbial inoculants and the liquid media.

Figure 1C:
Figure 1D:
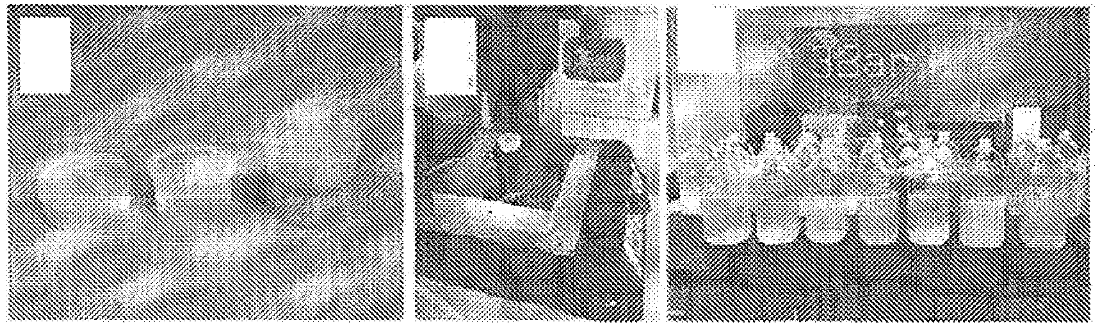

FIG. 1C is a photograph showing a system 10 before use (left), and two days after activation (right) showing turbidity which is as indication of late log/early stationary phase microbial growth.

Gas Permeable Member

A gas permeable member is generally understood to be a biocompatible material capable of allowing transfer of gas into and out of an enclosed space. The gas permeable member can be either liquid permeable or impermeable, hydrophobic or hydrophilic, porous or non porous. Thickness can range above or below 0.25 mm. The choice depends on the specific application. In one embodiment, the gas permeable member 34 is liquid impermeable so as to prevent leakage of media and to prevent contaminants from entering the chambers. As a general guideline, the gas permeability of a given member should be considered in addition to the interaction of the member with either cells or protein structures. Liquid impermeable members of equivalent thickness will establish various steady state oxygen tensions at the cell/film interface. FEP Teflon, silicone, and silicone polycarbonate copolymers will establish higher oxygen tension than polyethylene, polycarbonate, polypropylene, polysulfone, or polypropylene.

Package Container Size and Shape

The dimensions and shape of the system itself, and the first chamber and the second chamber, can be varied to suit the needs of expense, manufacturer and specific applications. Along with gas exchange and mixing, other criteria to selecting a shape include shear force and cell yield. In certain embodiments, a system that is longer than wider is preferred. A wide range of interior volumes is contemplated, ranging from 0.1 L to 200 L or more. In certain embodiments, the second chamber has an interior volume of about 0.05 L-100 L. In one embodiment such interior volume is 1. In another embodiment, the interior volume of the second chamber is about 50 mL to about 500 mL. Smaller sized second chamber are especially appropriate for small-scale usage, such as personal gardening, landscaping, and nurseries. Larger sized second chamber are especially appropriate for large scale farming operations and other commercial applications. The size of the first and/or second chambers, the amount of media and microbial cultures can be tailored to the target consumer and its intended end-use application. Although rectangular and bottle-like shapes are illustrated in the figures, these shapes are meant to be illustrative and not limiting. Other shapes can also be utilized.

Fabrication Materials and Techniques

The packaging container is preferably formed from a suitable plastic substrate, such as, for exemplary purposes only, polypropylene or polyethylene, and with sufficient structural rigidity to prevent deformation, breakage and/or tearing of same during manufacturing and use. Preferred are plastics that do not scavenge oxygen. Alternatively a bag-in box-format where the external box provides suitable rigidity for the interior flexible bag can also be used.

The components of the system described herein can be fabricated from materials or substrates that are generally selected according to properties, such as reaction inertness, durability, expense, or the like. In certain embodiments, for example, components are fabricated from various polymeric materials such as, polytetrafluoroethylene (TEFLON™), polypropylene, polystyrene, polysulfone, polyethylene, polymethylpentene, polydimethylsiloxane (PDMS), polycarbonate, polyvinylchloride (PVC), polymethylmethacrylate (PMMA), or the like. Polymeric parts are typically economical to fabricate, which affords culture chamber disposability. Also, the components can be optionally fabricated from other materials including, e.g., glass, metal (e.g., stainless steel, anodized aluminum, etc.), silicon, or the like. For example, the first and second chambers can be optionally assembled from a combination of materials permanently or removably joined or fitted together.

Other components forming the system described herein can be optionally formed by various fabrication techniques or combinations of such techniques including, e.g., injection molding, cast molding, machining, embossing, extrusion, etching, or other techniques. These and other suitable fabrication techniques are generally known in the art and described in, e.g., Rosato, *Injection Molding Handbook*, 3rd Ed., Kluwer Academic Publishers (2000), *Fundamentals of Injection Molding*, W.J.T. Associates (2000), Whelan, *Injection Molding of Thermoplastics Materials*, Vol. 2, Chapman & Hall (1991), Fisher, *Extrusion of Plastics*, Halsted Press (1976), and Chung, *Extrusion of Polymers: Theory and Practice*, Hanser-Gardner Publications (2000), all of which are expressly incorporated herein by reference. After the chambers or other component parts are fabricated, they can be further processed, e.g., by coating surfaces with, e.g., a hydrophilic coating, a hydrophobic coating, or the like.

Dispensing Microbial Inoculants

Various methods are useful for the actual dispensing of the microbial inoculant from the presently described system. Thus, depending on the configuration of the system, alternative methods can be employed to affix and/or separate the first chamber from the second chamber. For example, following mixing and incubation of the microbial culture in the media to form the liquid "microbial inoculant," the first chamber can be optionally removed from the second chamber by unscrewing one chamber from the other. In an alternative example, the first and second chambers can snap together, and be removed when needed.

The microbial inoculants can be diluted directly from the first or second chambers. In one embodiment, either the first chamber or the second chamber can be configured to be attachable to a diluter or sprayer for dilution and application to seeds, soil, plants, or for whatever application the inoculant is to be used.

It is also to be understood that the microbial inoculant can be applied in a variety of manners. For example, the microbial inoculant can be directly applied to seeds. For example, leguminous plants form a large group of plants including vegetables of economic importance such as soybean, lucerne (alfalfa), peanut, peas, beans, and the like, and rhizobial inoculants applied to such leguminous seeds can colonize the rhizosphere and infect the roots of the plants, as they permeate into the radicular hairs and colonize the root, producing nodules. As a result of this symbiotic relation, plants can turn gaseous nitrogen into organic compounds of nitrogen through nitrogen fixation. The plants then can use these organic compounds to grow.

Thus, in another aspect, methods are provided herein for treating seeds or plants with a microbial inoculant. The method can generally include: producing a "fresh" or "late log/early stationary phase" liquid microbial inoculant, diluting such microbial inoculants to a desired cell density, and applying the microbial inoculants at a desired rate for maximal efficacy. In certain embodiments, the method can also include allowing the seeds to dry to an acceptable moisture content, so as to not interfere with germination of the seeds, and planting the seeds.

It is also to be understood that the amount of fresh, or log stage growth, microbial inoculants to be applied to the seeds varies. In exemplary applications, the application rates can range from about $10^3$ to about $10^7$ cells/seed. Spraying rates can vary from about $10^3$ cells/ml to about $10^7$ cells/ml. Prior to application of the microbial inoculants to the seeds, the liquid inoculant can be diluted to a cell number of 1,000 to about 10,000,000 colony-forming units (CFUs) per ml in the target diluent.

It is also to be understood that the desired amount of added moisture to seeds following application of the liquid inoculants can range from 0.1% to about 2%, with particular embodiments ranging from 0.3 to 0.8%. Too much moisture on the seeds can disrupt germination. One of ordinary skill in the art would know the ideal amount of inoculants to be added to the seeds depending on the microbe utilized, the species of seeds to be treated, and the soil conditions where the seeds are to be planted, to ensure maximum efficacy.

Kits for Culturing Fresh Microbial Inoculants

Also provided herein are kits for culturing fresh microbial inoculants. The kit can generally include a system presently described that has a specific amount of stable microbial inoculant and media, and instructions on usage, preferred incubation times, incubation temperatures, growth rates, application rates, dilutions, and spraying rates. The kits can have both proprietary and non-proprietary microbes and/or media, microbes specific to a particular soil or region in which seeds are to be planted, or plants being treated are grown. Kits can be custom prepared for the specific needs of the grower. Thus, the kits provide a ready to use, simple method for an operator untrained in the microbiological arts to produce fresh, efficient microbial inoculants for application to seeds, plants, soils, and other intended uses of the microbial inoculants in the field.

Additional Applications of Fresh Microbial Inoculants

It is also to be understood that the presently described system and methods provided herein are not limited for use in agricultural, gardening and landscaping related applications, but can be used for any application where rapidly growing microbes having greater viability and efficacy are desired. Examples of such applications include, but are not limited to, silage inoculants, animal and human probiotics, food production, environmental remediation to toxic chemicals and radioactive compounds, composting of a broad range of waste materials, and biological control of pests. Some common microbial genera that could benefit from this approach include, but are not limited to: *Achromobacter, Aerococcus, Atopobium, Bifidobactrium, Brevundimonas, Brochothrix, Carnobacterium, Enterococcus, Galactomyces, Lactobacillus, Pseudomonas, Saccharomyces, Stentotrophomonas, Streptococcus*, and *Weisella,*

Certain embodiments of the present invention are defined in the Examples herein. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

EXAMPLES

The examples below demonstrate an embodiment of the system, method, and kit claimed below wherein the microbes used were phlD+ pseudomonad strains, a group of beneficial soil bacteria previously shown to be capable of significantly affecting the growth and health of different plant species (Weller et al 2002, McSpadden Gardener et al. 2005, Raudales and McSpadden Gardener 2009). Other beneficial soil bacteria belonging to the genera *Azospirillum, Bacillus, Mitsuaria*, and *Pseudomonas* have been tested in this system with similar results.

Example 1—Growth of Bacteria in a Bioreactor

Several different bacteria were grown on liquid media to stationary phase and inoculated onto a solid matrix of ground soybean seeds. Under axenic conditions, the bacteria were applied separately to the solid matrix at a rate of 1 ml per 100 g of ground seed with stirring and sealed in a plastic chamber with 20% headspace of ambient air. The first chamber was attached to a second chamber containing pure mineral water. After four days of storage, the contents of chamber 1 were released into chamber 2 by disruption of the interposing plastic membrane by virtue of an internal spike. The suspension was gently mixed and the bioreactor set on its side at room temperature. After 1 to 3 days, turbid growth was observed in chamber 2 (FIG. 1C).

Figure 3:
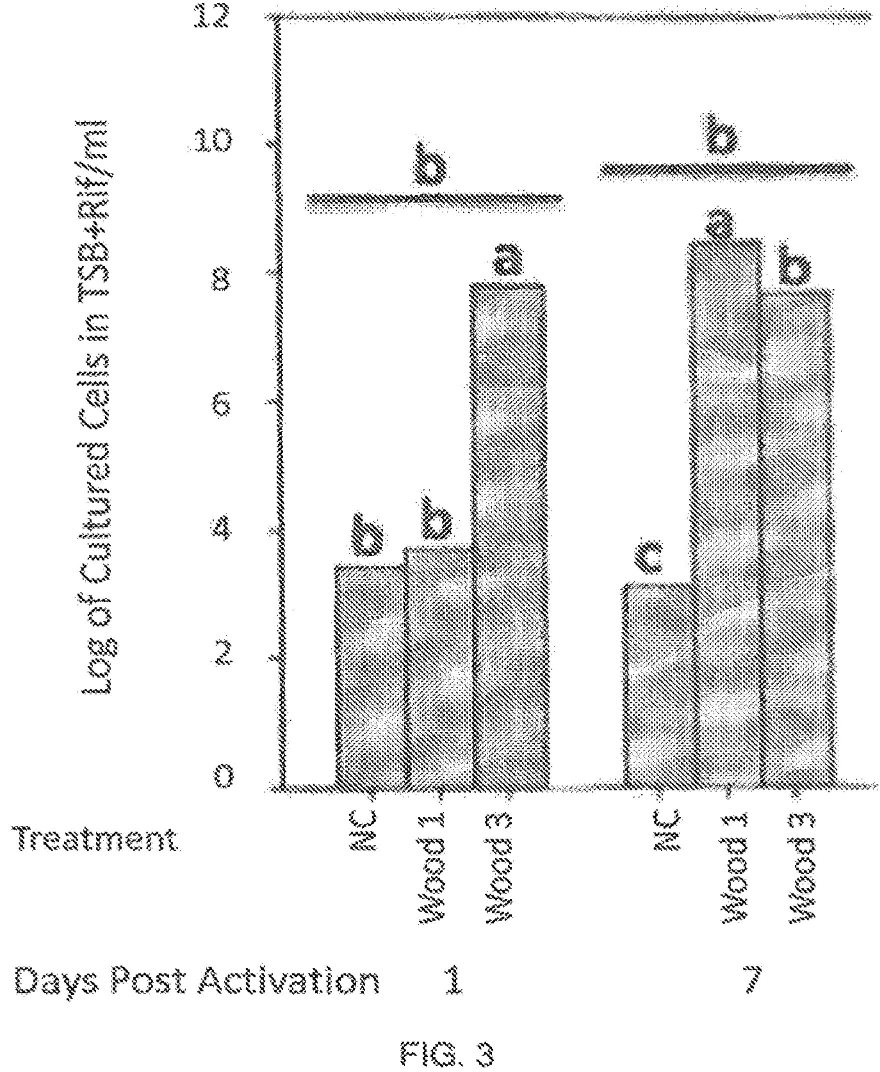
FIG. 3: Bar graphs depicting of the growth of two bacterial strains (Wood1 and Wood3) used in the bioreactor system described herein. Bioreactors were loaded with different bacteria in chamber 1 on a solid matrix of ground soybean seeds. The bioreactors were subsequently activated and handled according to label instructions (FIG. 2). Graphs show cell counts recovered from the media of chamber 2 after either one day or seven days of incubation at ambient room temperature for both strains. Both strains reached a saturating (i.e. completion of log phase) growth sometime between 1 and 7 days after activation. Repeated trials with various exemplary bacteria demonstrated that saturating growth can reliably occur between 1 and 3 days after activation.

FIG. 3 provides representative quantitative data on the actual number of culturable cell counts obtained from uninoculated (NC) as well as inoculated (Wood1 and Wood3) bioreactors on semi-selective media after 1 and 7 days. Direct microscopic counts confirmed the number of cultured cells to saturate at ~$10^8$ cells per ml. The activity of the cultures was evidenced by the occurrence of actively swimming cells for up to two weeks following activation. The actual number of cells obtained depends on the strain, the amount of solid matrix used, and its composition. Such data demonstrate that a bioreactor as described herein can be used to develop active bacterial cultures on demand.

Example 2—Responses of Soybeans to the Application of Beneficial Bacterial Seed Treatments Using the Bioreactor Described Herein Bioreactors were prepared using different strains of bacteria previously shown to have beneficial effects on plant growth, health, and/or yield (see Table 1). Inoculation of chamber 1 and assembly of the bioreactors were conducted as described above. The bioreactors were stored at room temperature for five to nine weeks before use, depending on planting date. Six different bioreactors, each containing a single inoculant strain belonging to the genus *Pseudomonas, Mitsuaria, Bacillus*, or *Azospirillum* were activated each week and their contents were used to treat seed between three and seven days following activation according to label instructions (FIG. 2). Treated seeds were planted in a replicated block design (n=4) alongside control treatments at six different locations throughout Ohio. Comparisons of stand counts and yields were conducted during the growing season and at harvest, respectively (FIG. 4).

Results from this multi site field trial are summarized in FIG. 4. Five of the six experimentals (Strain 1 to 6) outperformed the uninoculated control (Control). The percentage of sites where a positive response relative to the negative control were observed ranged from 50 to 83%, which compared favorably to the 50% stand response to the chemical seed treatment. Average stand improvements across all six test sites, relative to the untreated control, ranged from 0.2 to 3.3%.

TABLE 1

Descriptions of bacterial strains having beneficial effects on plant growth, health, and/or yield.

| Strain Number | Description |
|---|---|
| Strain 1 | *Pseudomonas* sp. strain Exp1 (i.e. Wood3) |
| Strain 2 | *Pseudomonas* sp. strain Exp2 (i.e. Wood1) |
| Strain 3 | *Mitsuaria* sp. strain Exp3 |
| Strain 4 | *Bacillus* sp. strain Exp4 |
| Strain 5 | *Pseudomonas* sp. strain Exp5 |
| Strain 6 | *Pseudomonas* sp. strain Exp6 |
| Strain 7 | *Azospirillum* sp. strain Exp7 |

Average yields for 5 of the 6 bioreactor-supplied seed treatments exceeded that of the control by 1.2 to 2.5%. Such yield increases were as large or larger than that provided by an industry standard seed treatment (Ind Std) called TMGerm. Additionally, a bioreactor-supplied seed treatment combined additively to that industry standard seed treatment provided even greater yield increases of 2.0% more than the TMGerm-treated seed alone and 3.2% more yield than the untreated control.

These data demonstrate the utility of the prototype bioreactor in delivering beneficial soil bacteria to leguminous crops.

Example 3—Responses of Corn to the Application of Beneficial Bacterial Seed Treatments Using the Bioreactor Described Herein A separate study, similar to the one described for soybeans above, was conducted on corn. Bioreactors were prepared using different strains of bacteria previously shown to have beneficial effects on plant growth, health, and/or yield. Inoculation, assembly, and storage of the bioreactors were conducted as described above in Example 2. Four different bioreactors, each containing a single inoculant strain belonging to the genus *Pseudomonas, Mitsuaria*, or *Azospirillum* were activated each week and their contents were used to treat seed between three and seven days following activation according to label instructions (FIG. 2). Treated seeds were planted and the growing corn crop assessed at six different locations throughout Ohio.

On corn, bioreactors inoculated with the experimental bacterial strains (Strain 1, 2, 3, and 7) outperformed the control treatment in terms of stands and yields (FIG. 5). On average, corn treated with inoculants made from the bioreactors had higher stands (0.8 to 8.1×100 plants per acre) and higher yields (5.2 to 10.2 bu/acre). These represent stand increases of 0.2 to 2.3% and yield increases of 2.0 to 4.6% across the six test sites.

Additionally, the bioreactor delivered results that exceeded those by commercially available inoculants. For instance, yield increases for three of the four test treatments were as good or better than an industry standard (Ind Std) seed treatment (TMGerm). Additionally, when Strain 1 was combined with the industry standard seed treatment, further increases in average stands and yields were observed. Furthermore, while the commercially available formulant of strain 7 (Comm7) did increase the six site average stands and yields of corn, even higher stands and yields were obtained with the same strain formulated in the prototype bioreactor (Strain7) demonstrating that the bioreactor can deliver a more effective dose of a beneficial microbial inoculant. These data demonstrate the utility of the prototype bioreactor in delivering beneficial soil bacteria to grain crops.

Overall, these Examples indicate that fresh microbial inoculants, using the system described herein, when applied to seed, may be used to generally improve crop performance.

Example 4—On-Farm Seed Treatment of Corn

Because of the limited viability of many types of beneficial bacteria, under extended periods of dryness, seed treatment at the seed bagging and distribution level may be not practical. In such situations, an alternate approach to biological seed treatment may be more appropriate for large commercial development. For example, use of a larger rotary mixer (e.g., a 50 gallon mixer) on-site could speed treatment and ensure good coverage for larger seed batches for whole farm use.
Alternatively, the grower could dilute the bacterial solution into a liquid that is applied in-furrow from the planter, such as water or liquid starter fertilizer. One such application (FIG. 6) resulted in an increased corn crop yield of 4.6% compared to the untreated control.

Thus, the system and methods described herein provide a low cost, effective method of producing a fresh, contaminant-free, more effective microbial inoculates in the field that can be performed by a worker unskilled in the microbiological arts.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

All publications, including patents and non-patent literature, referred to in this specification are expressly incorporated by reference herein. Citation of the any of the documents recited herein is not intended as an admission that any of the foregoing is pertinent prior art. All statements as to the date or representation as to the contents of these documents is based on the information available to the applicant and does not constitute any admission as to the correctness of the dates or contents of these documents.

What is claimed is:

1. A method of promoting plant growth, comprising:

(A) activating a microbial inoculant system to form a liquid inoculant, the system comprising:

a sealed bioreactor comprising a rigid container enclosing a first chamber and a second chamber separated by at least one dividing member, wherein the first chamber is connected to the second chamber;

a predetermined amount of a stable microbial culture in the first chamber;

a predetermined amount of a liquid medium in the second chamber;

wherein at least one of the first chamber and the second chamber comprises at least one gas permeable member, and wherein activating comprises:

(1) disrupting the integrity of the dividing member;

(2) introducing the microbes of the first chamber into the second chamber; and (3) culturing the introduced microbes to a log phase growth stage in the sealed bioreactor, thereby forming a liquid inoculant; and (B) applying the liquid inoculant to a seed.

2. The method of claim 1, further comprising diluting the liquid inoculant before applying.

3. The method of claim 2, wherein the diluted liquid inoculant contains 1,000 to about 10,000,000 colony-forming units (CFUs) per ml.

4. The method of claim 1, further comprising planting the seeds.

5. The method of claim 1, wherein applying adds 0.1% to about 2% moisture to the seed.

6. The method of claim 1, wherein about $10^3$ to about $10^7$ cells/seed are applied to the seed.

7. The method of claim 1, further comprising allowing the seed to dry to a predetermined moisture content after applying the liquid inoculant.

8. The method of claim 1, wherein applying comprises spraying.

9. The method of claim 8, wherein the liquid inoculant is sprayed at a rate of $10^3$ cells/ml to about $10^7$ cells/ml.

10. The method of claim 1, wherein the seed is selected from the group consisting of petunia, tomato, legume, or grain crop seeds.

11. The method of claim 1, wherein the dividing member is disrupted by piercing, tearing, cutting, breaking, puncturing, rupturing, dissolving, or moving the dividing member.

12. The method of claim 1, wherein the rigid container includes sidewalls and culturing includes storing the bioreactor on its side.

13. The method of claim 1, wherein at least one of the first chamber and the second chamber includes at least one access port for connection to a delivery device.

14. The method of claim 1, wherein the second chamber has an interior volume of from about 50 mL to about 500 mL.

15. The method of claim 1, wherein the second chamber has an interior volume of from about 0.5 L to about 100 L.

16. The method of claim 1, wherein the first chamber and the second chamber are fabricated, at least in part, from a polymeric material.

17. The method of claim 1, wherein the rigid container prevents deformation, breakage, and/or tearing of the sealed bioreactor during manufacturing and use.

18. The method of claim 1, wherein the rigid container is fabricated from polypropylene or polyethylene.

19. The method of claim 1, wherein culturing the introduced microbes comprises incubating the bioreactor for a period of from 1 day to 14 days at a temperature of from about 20° C. to about 50° C.

20. The method of claim 1, wherein oxygen is present in the second chamber, as a percentage of total gas in the second chamber, in a percentage of between 5% to 25% oxygen.

* * * * *